US005458618A

United States Patent [19]

Steinke

[11] Patent Number: 5,458,618

[45] Date of Patent: Oct. 17, 1995

[54] BODY MOTION GENERATING DEVICE HAVING HIGH INERTIAL POWER TRAIN

[76] Inventor: James M. Steinke, 143 Foxridge Run, Longwood, Fla. 32750

[21] Appl. No.: 254,972

[22] Filed: Jun. 7, 1994

[51] Int. Cl.$^{6}$ .................................................. A61F 5/00

[52] U.S. Cl. ........................................ 606/242; 606/243

[58] Field of Search ................................ 606/241–245; 5/613, 617, 636

[56] References Cited

U.S. PATENT DOCUMENTS

| | | | |
|---|---|---|---|
| 5,123,916 | 6/1992 | Riddle et al. | 606/242 X |
| 5,158,568 | 10/1992 | Riddle et al. | 606/242 |
| 5,171,260 | 12/1992 | McIlwain | 606/243 |
| 5,282,835 | 2/1994 | Wright et al. | 606/242 |
| 5,320,640 | 6/1994 | Riddle et al. | 606/242 |
| 5,320,641 | 6/1994 | Riddle et al. | 606/243 |

*Primary Examiner*—Peter A. Aschenbrenner

[57] ABSTRACT

A passive body motion generating table for therapeutically exercising a lumbar recovering patients body, the table having a pivotally mounted leg support section, a pivotally mounted upper body support section, and a stationary lumbar support section, the pivotally mounted sections being pivotally movable in a generally vertically oriented arc by means of a power mechanism which does not employ drive belts, chains or the like, but rather direct bearing-to-rod linkage, wherein the linkage is also constructed to provide asymetric, adjustable pivotal travel of the pivotal support sections above and below a horizontal plane, and further to provide for adjustment of the degree of travel of the pivotal support sections.

5 Claims, 7 Drawing Sheets

BODY MOTION GENERATING DEVICE HAVING HIGH INERTIAL POWER TRAIN

FIELD OF INVENTION

The present invention concerns therapeutic, passive body-motion generating devices and therapeutic motion procedure, particularly those devices and procedures which are used for human body rehabilitation purposes and which require little or no physical effort of the patient for producing the motion. In particular this invention concerns a unique power train for a body motion generating device or apparatus such as shown for example, in U.S. Pat. Nos.: 5,258,019; 5,123,916; 5,282,835; 5,171,280; 2,598,204; 2,152,431; and 4,723,537, and particularly such apparatus which raises or lowers the upper torso and the legs in a simultaneous controlled manner while maintaining the lower lumbar region in a substantially passive condition.

BACKGROUND OF THE INVENTION

Patients who have experienced impact, twist or other damage, or who have undergone serious surgery of the back, e.g., of the lumbar region, particularly of the spine, are typically required, or at least advised, to essentially immobilize the back by maintaining a prone position for extended periods of time. In many cases however it has been recognized that some, even though slight motion of the damaged and/or adjacent areas of the back during recovery or rehabilitation has beneficial effects, for example, in enhancing blood flow to the area, in helping to maintain muscle strength and tone, and in maintaining a general feeling of activity and well-being in the patient.

DISCUSSION OF THE PRIOR ART

Many devices and apparatus for imparting motion to various parts of the body have been devised and include those shown in the aforesaid U.S. patents and in U.S. Pat. Nos.: 4,802,462; 4,827,913; 3,039,456; 4,716,889; 3,060,926; 3,370,584; 4,860,734; 4,795,150; 4,834,073; and 3,071,130, the general diclosures of utility and structure such as bases or supporting frames, body support means, cushioned body support pads or platforms, electrical control systems, or the like contained in all of said patents, being incorporated herein by reference.

These prior art devices are no doubt therapeutically effective for the specific situations for which are designed, however, none of them relate to the particular objectives of the present invention. For example, these prior passive motion apparatus have a gravitational aspect to their function, which may lead to accidents for the patient. For example, where injury or surgery has occurred with respect to the lumbar or other regions of the spine near or proximate thereto, any position of the body other than essentially horizontal can place a gravitational burden on the spine and adjacent tissue tending to compact the same, likely with anti-therapeutic effect. Moreover, with respect to the aforesaid first four patents the power or drive trains typically employ chain devices or hydraulic cylinder means for imparting reciprocating motion to the body support members thereof.

A serious problem associated with such drive means is that when a structural failure occurs, for example, a chain link breaks or a sprocket slips, or a hydraulic cylinder seal ruptures or some other loss of hydraulic pressure occurs, or through looseness in the drive linkage, the body support members of the device may fall, even slightly under the force of gravity and cause injury to the patient, particularly to the injured area which the exercise or motion is intended to rehabilitate. This is especially the case for patients who are undergoing lower back rehabilitation and who find it difficult to withstand sudden and excessive flexure or other forces on the back. Also, in certain ones of these prior drive means, when power thereto is terminated, a patient's weight alone on the pivotable table may cause the drive means to reverse its direction and allow the table to drop to an undesirable position.

Objects, therefore, of the present invention are: to provide an exceptionally safe passive body-motion device or apparatus which can lightly and controllably move or flex regions of the back immediately adjacent an impaired segment thereof, and also the segment itself if desired, without placing a gravitational or other force burden thereon, while maintaining the segment in a substantially passive condition, and while imparting the salutory effects of the motion to the impaired segment; to provide such apparatus with motion degree adjustability, particularly via automatic or semi-automatic mechanism, patient accessibility to drive control mechanism and with enhanced safety features; to provide a passive body-motion procedure which maintains substantial passivity of a back region being rehabilitated while providing intracorporeal activity to said region through the passive motion of adjacent back regions; to provide such apparatus with structural compactness and storage or transportation fold-up features; to maximize the simplicity of construction and operation of such apparatus; to provide a drive or power train for such device or apparatus wherein the power or drive train thereof has inherent, high inertial resistance to free motion, i.e., to non-powered motion, of the body support members of the device; to provide such power train with markedly simplified structure of improved structural strength and longevity; to provide such apparatus with improved motion control mechanisms for adjusting the degree of motion of the body support members, said mechanisms also empolying high inertial adjustment structures; to provide said power train and motion control mechanisms with sufficient inherent inertia to essentially instantly cease motion of said body support members upon the development of a structural defect or excessive looseness in said power train; and to provide an electrical switch means for mounting on said apparatus whereby irregular or defective motion of said body support members is detected thereby and results in immediate termination of power to said power train.

BRIEF SUMMARY OF THE INVENTION

These and further objects hereinafter appearing have been attained in accordance with the present invention which is defined as a passive body-motion generating apparatus for a lumbar region, back segment, comprising base means, lower body support means, upper body support means, the top of each said support means providing body contact surface means, a stationary, substantially flat lumbar region, back segment support means on said base means lying intermediate said pivot end portions, said back segment support means having a width of from about 2 to about 12 inches, preferably from about three to about seven inches, said body support means each having a pivot end portion lying substantially adjacent an opposite side of said back segment support means, pivot means cooperatively mounted on each said pivot end portion and said base means for allowing independent rotative motion of each said lower and upper body support means through an arc sector, the pivot axes of said pivot means being substantially parallel, and bearing mounted power train means on said base means in operative association with both said body support means for imparting simultaneous rotative force thereto, said power train means having a longitudinal directional field, a vertical directional field and a lateral directional field and comprising first power means mounted on said apparatus and having drive shaft means, drive crank arm means affixed to said shaft means, crank link means having one end pivotally connected to said crank arm means and its other end pivotally connected to sector plate means, said plate means being pivotally mounted on said apparatus, adjustable pivot means mounted on said plate means for position adjustment within each of said longitundinal and vertical directional fields, swing link means having one end pivotally connected to said adjustable pivot means, first lever means pivotally mounted on said apparatus and having a first driven arm means and a first drive arm means, the other end of said swing link means being pivotally connected to said driven arm means, first lift link means having one end pivotally connected to said first drive arm means and having its other end pivotaly connected to one of said lower or upper body support means, second lever means pivotally mounted on said apparatus and having a second driven arm means and a second drive arm means, drag link means having one end pivotally connected to said second drive arm means and having its other end pivotally connected to said first driven arm means, second lift link means having one end pivotally connected to said second drive arm means and having its other end pivotally connected to the other of said lower or upper body support means, wherein the pivot axes of all of said pivotal connections are within said lateral directional field.

In certain preferred embodiments:

(1) said first power means is provided with motion resistance means giving a constant inertial, reverse arrest drag of at least about 150 pounds as measured at the lift point of each said body support means;

(2) the adjustable pivot means is of the sliding nut type and is moved within a substantially vertical track support on said sector plate means by electrically operated second power means;

(3) the track support is adjustably mounted on said sector plate means for adjustment substantially within said longitudinal component; and (4) the motion of adjustment of said track support on said sector plate means is along a segment of the pivotal arc of said sector plate.

BRIEF DESCRIPTION OF THE DRAWINGS

The invention will be further understood from the accompanying drawings of preferred embodiments and a description thereof wherein the various figures are not necess drawn to scale or proportion.

DETAILED DESCRIPTION OF THE DRAWINGS

Figures 1, 2:
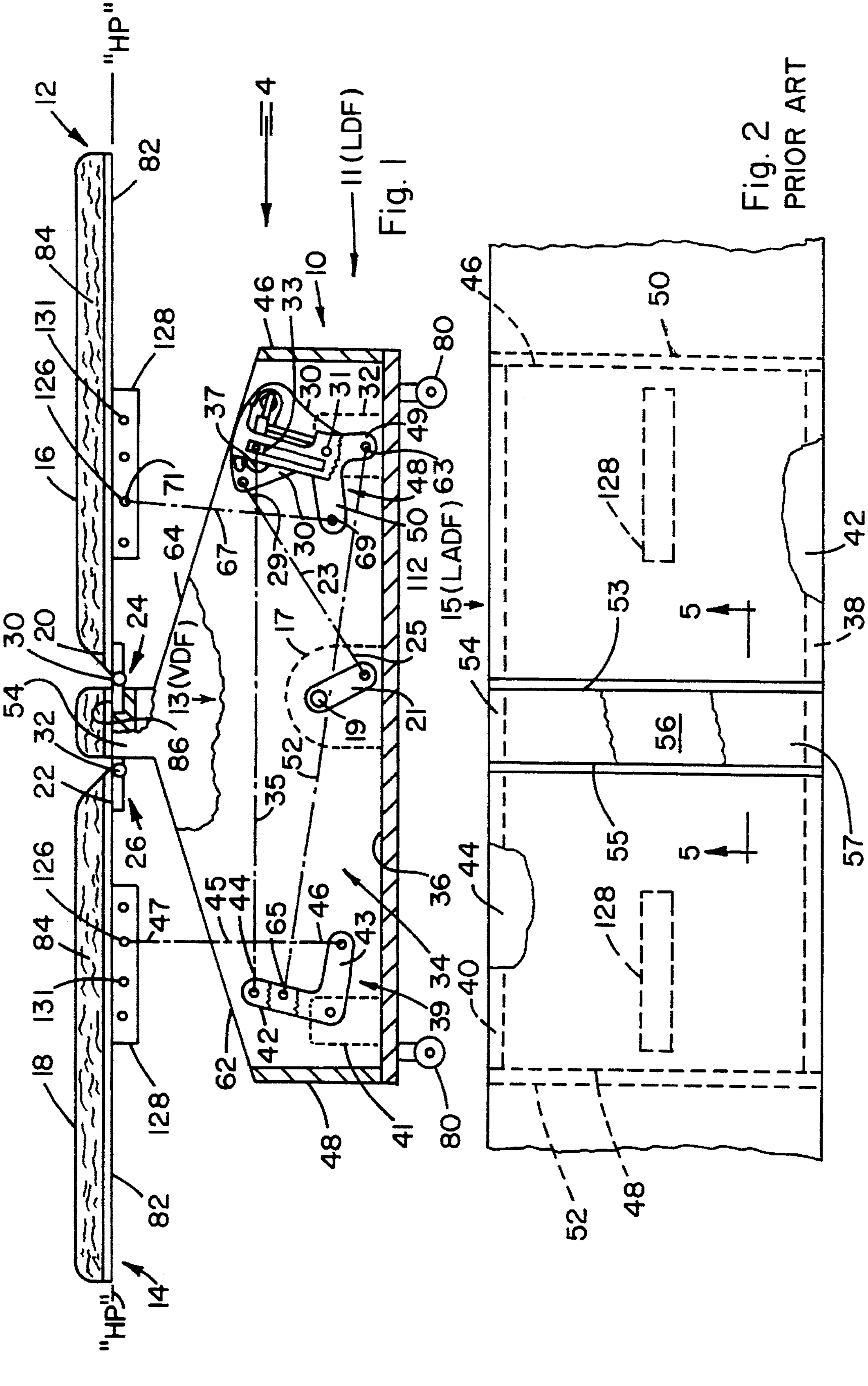
Fig. 2 PRIOR ART
FIG. 1 is a side view of the apparatus with the side wall removed to show details of the power train means.
FIGS. 2–6 are substantially taken directly from U.S. Pat. No. 5,171,260.
Figure 3:
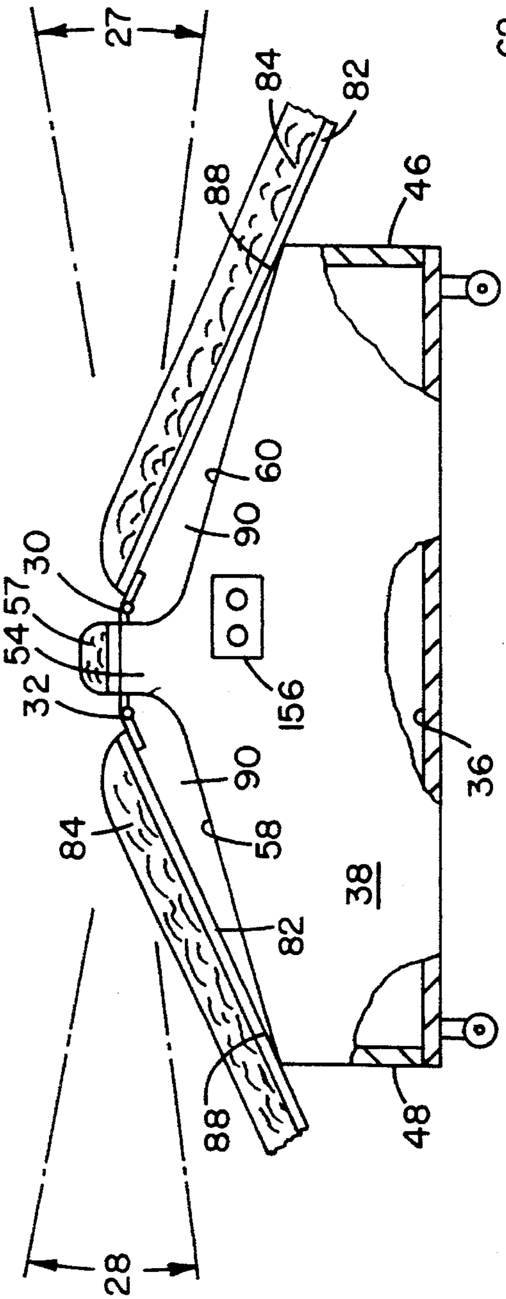
Fig. 3 PRIOR ART

Referring to the drawings and with reference to the claims hereof, the present invention is defined in its broad sense as a passive body motion generating apparatus for a lumbar region back segment comprising base means 10, lower body support means 12, upper body support means 14, the tops of said support means providing body contact surface means 16 and 18 respectively, said body support means having pivot end portions 20, 22 lying substantially adjacent opposite sides, 53, 55 respectively of a back segment support means 56, stationary, substantially flat lumbar region, back segment support means 56 on said base means lying intermediate said pivot end portions, said back segment support means 56 having a width of from about 2 to about 12 inches, preferably from about three to about seven inches, pivot means 24, 26 cooperatively mounted on said pivot end portions and said base means for allowing rotative motion of each said support means 12, 14 through arc sectors 27, 28 respectively, the pivot axes of said pivot means being substantially parallel and in proximity to each other, and bearing mounted power train means generally designated 34 on said base means, linkage means pivotally mounted on said apparatus for pivotal motion with respect to said base means and both said body support means for imparting simultaneous rotative force to said both support means, said power train means having a longitudinal directional field 11, (LDF) a vertical directional field 13 (VDF) and a lateral directional field 15 (LADF) and comprising first power means 17 mounted on said apparatus and having drive shaft means 19, drive crank arm means 21 affixed to said shaft means, said linkage means comprising crank link means 23 having one end 25 pivotally connected to said crank arm means and having its other end 29 pivotally connected to sector plate means 30, said plate means being pivotally mounted by shaft means 31 on a base portion 32 of said apparatus, preferably by welding the plate means to the shaft means and mounting the shaft means in pillow blocks 115 affixed to the base means, adjustable pivot means 33 mounted on said plate means for position adjustment within each of said longitundinal and vertical directional fields, swing link means 35 having one end 37 pivotally connected to said adjustable pivot means, first lever means 39 pivotally mounted on a base portion 41 of said apparatus and having a first driven arm means 42 and a first drive arm means 43, the other end 44 of said swing link means being pivotally connected to said first driven arm means, first lift link means 45 having one end 46 pivotally connected to said first drive arm means and having its other end 47 pivotaly connected to one of said lower or upper body support means, second lever means 48 pivotally mounted on said apparatus and having a second driven arm means 49 and a second drive arm means 50, drag link means 52 having one end 63 pivotally connected to said second driven arm means and having its other end 65 pivotally connected to said first driven arm means, and second lift link means 67 having one end 69 pivotally connected to said second drive arm means and having its other end 71 pivotally connected to the other of said lower or upper body support means, wherein the pivot axes of all of said pivotal connections are within said lateral directional field.

The general construction of the present apparatus aside from the present power train and linkage is shown in FIGS. 1–6 of U.S. Pat. No. 5,171,260, the disclosure of which with regard to said general construction is hereby incorporated herein by reference.

Figure 6:
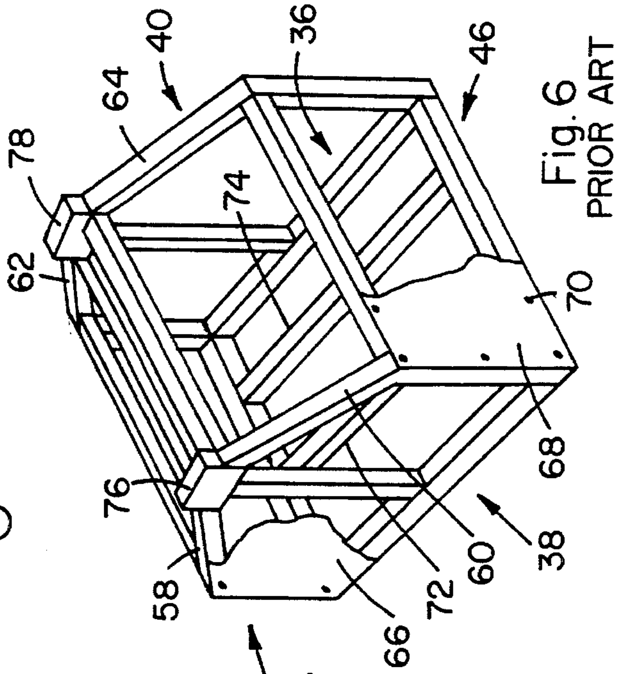
Fig. 6 PRIOR ART

The base means 10 can be of any configuration and construction, however, the base as shown in the drawings has certain preferred features. As shown, the base comprises a floor 36 which may of solid material such as metal sheet, plywood, fiberboard, fiberglass sheet, or the like, or preferably, as shown in FIG. 6, constructed as a framework, e.g., from sections of square or rectangular metal tubing welded together in such array as to provide bolt receiving supports for mounting the pillow blocks and power means such as electric motor/worm-gear reduction units of the drive means in known manner. Sidewalls 38 and 40 are affixed to the base along the longitudinal edges 42, 44 respectively thereof, and endwalls 46 and 48 are affixed to the base along the lateral edges 50, 52 respectively thereof, by any suitable means such as screws, bolts, or other conventional fasteners.

Each sidewall of the base means is preferably configured and structured to provide substantially raised central portions generally indicated as 54 which are affixed to and bridged by lateral support or back segment support means 56 which provides a base segment to which body supports 12 and 14 are affixed by means of the hinge or pivot means 24 and 26. The upper edge portions 58, 60 and 62, 64 respectively of sidewalls 38 and 40 preferably are sloped downwardly from portions 54 to allow a semi fold-up position of the body supports as described hereinafter in greater detail.

The upper ends 47, 71 of the lift links are rotationally secured to brackets such as 128 by shafts 129 which may be removably secured in place by pins 130 (see FIG. 4) or the like slid through apertures in the shafts. The brackets are secured to the body supports by any suitable means such as screws, and are preferably provided with a series of rod mounting apertures 131 such that the angle at which the lift links are affixed thereto can be adjusted to provide further adjustment of the arc segment or angle through which each body can be rotated.

Shown in FIG. 6 is a preferred embodiment of the base means construction comprising welded together steel tubing sections to provide the side walls, end walls and floor which are indicated generally by their respective characters. These metal sections are shown in exaggerated thicknesses for clarity, however, an adequate strength thereof must be provided to support the weight of very large persons. In this regard, additional diagonal bracing or the like connecting these sections may be provided as necessary. Portions of the sidewall and endwall facades 66 and 68 are shown in FIG. 6 and preferably comprise a cushioned, vinyl covered, highly attractive upholstery covering of about ¼ to ⅜ in. thickness mounted on a fiberboard or the like backing of about ⅛ in. thickness. These facades are attached by any suitable means such as metal clips or screws 70 to the metal tubing sections. The tubing sections 72 and 74 spanning the floor provide the necessary rigid supporting structure for mounting the drive train means as hereinafter described. The lateral support means 56 is not shown in FIG. 6 but may comprise a metal or wood plank or the like spanning and affixed to the tops 76, 78 of raised portions 54 by bolts or the like. The base is preferably provided with caster wheels 80 or the equivalent to allow easy movement and relocation of the apparatus.

Figure 18:
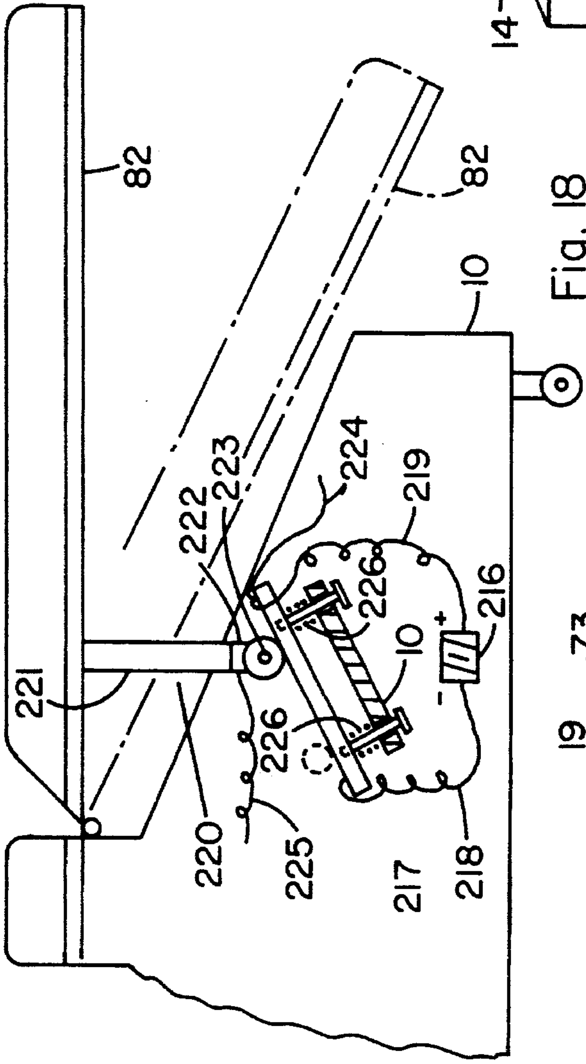
FIG. 18 is a schematic view of a safety mechanism for the present apparatus.
Figure 20:
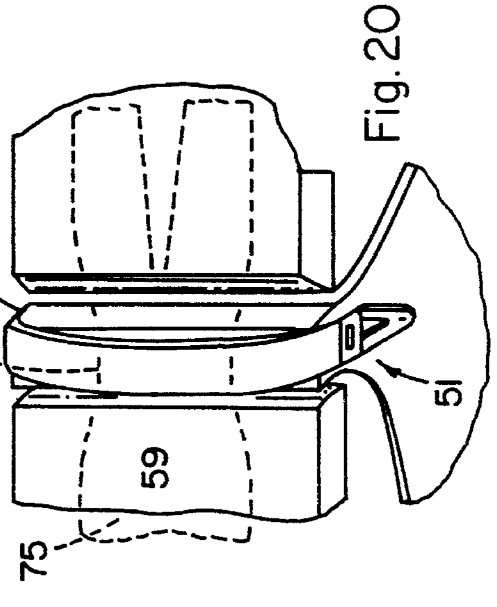
FIG. 20 shows the arrangement of the present apparatus and patient being treated.

The lower and upper body support means 12 and 14 are essentially identical in construction and interchangeable with respect to the body portion, i.e., upper or lower, whichever each one supports. Each is comprised of a rigid, substantially flat bed member 82 and a cushion or pad 84, preferably having an attractive vinyl covering and affixed to the bed member in any conventional manner. Each bed member is affixed at its pivot end portion to one section of its pivot means 24 or 26, which e.g., can comprise a hinge such as 85 shown in FIG. 5, which extends substantially across the width of the pad, the other section of the pivot means being affixed to lateral support means 56 in any suitable manner such as by screws, bolts or the like, and preferably to the top 86 thereof, to allow the body support means to readily pivot and cycle through its aforesaid arc sector. The arc sector angle can be, e.g., 50 degrees on either side of the horizontal plane "HP", but is preferably up to about 25 degrees below and 45 degrees above said plane. These body supports are, of course, adequately dimensioned to accommodate large patients and typically are from 3–4 ft. in width and 3–5 ft. in length. The lateral support means 56 and its cushion or pad 57 can be varied in width, for example, 2–12 inches, depending, on the area of the back which is intended to remain substantially passive during the rotative cyclical motion of the lower and upper body supports. Typically and preferably the width of this support means is from about 3–7 inches. In a preferred embodiment of the invention, a safety hold-down or body segment stabilizing strap means 59 of suitable material, e.g., padded vinyl, such as shown in FIG. 18 is provided and may be permanently attached at one end 73 to one side of the base and attachable to the other side of the base by, e.g., adjustable auto safety belt buckle means 51. In use, the strap is tensioned fairly tightly across the body 75 shown in dotted outline in the area of the lumbar region 61 and maintains, when desired, substantial inflexibility and immobilization of the back segment under treatment.

It is particularly noted that the outer extremities 88 of upper edge portions 58, 60, 62 and 64 of the sidewalls provide a limiting stop means for downward rotation of the body supports such as occurs when the apparatus is placed in the aforesaid semi-folded condition, but also in the event of failure or dislocation of the drive train linkage. In regard to the latter event, gaps 90 are provided between the upper edge portions of the sidewalls and the body supports to prevent damage to a patients hands or fingers which inadvertently may lave been placed under the body support edges during the exercise procedure.

As seen more clearly from FIG. 1, the pivot end portions of the support pads 16 and 18 are preferably bevelled such that upward rotation of the support means will not be restricted, and also to provide a degree of isolation of the lateral support means from the main body support means to enhance the immobilization effect of the lateral or lumbar support.

Figure 8:
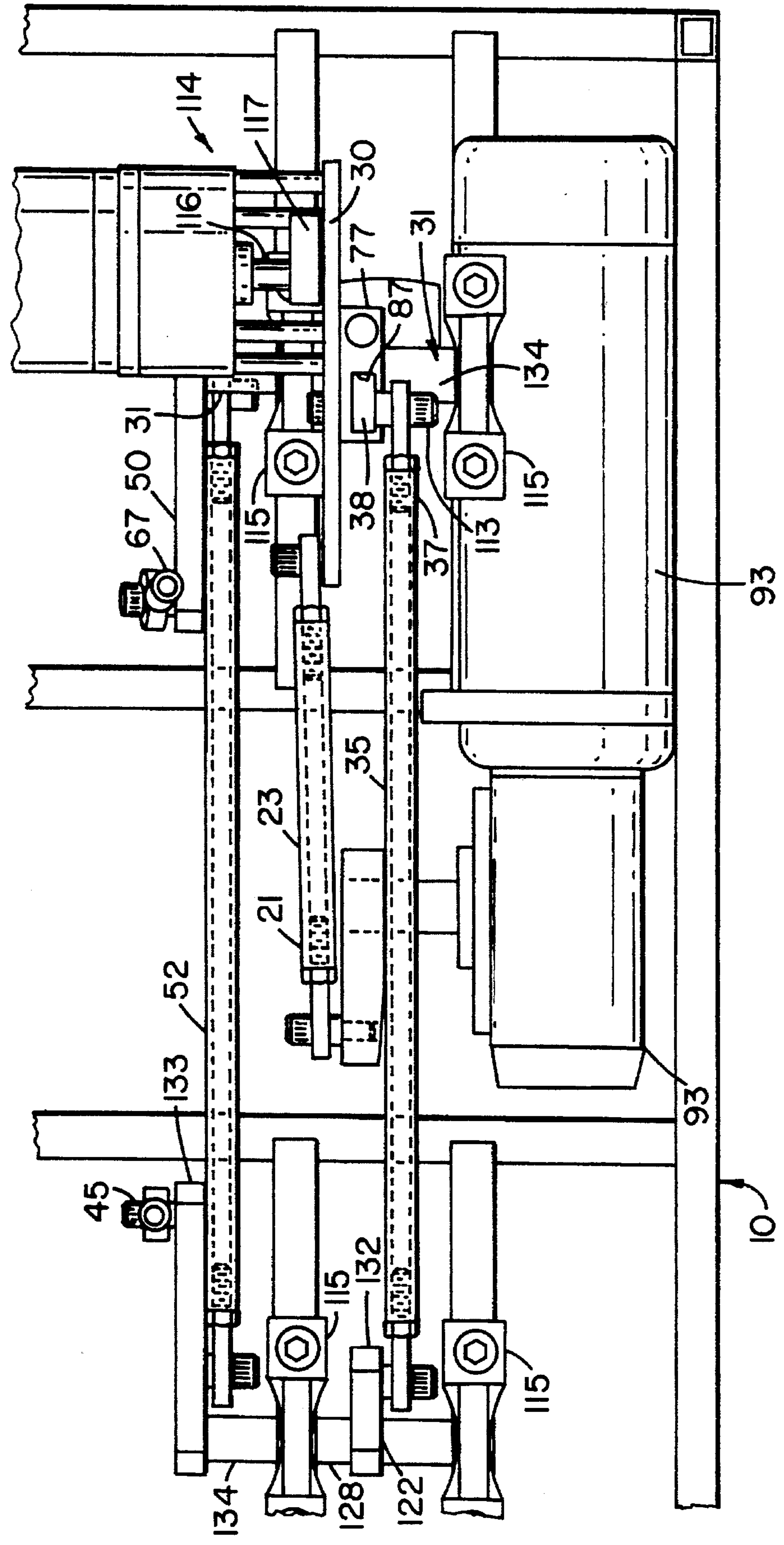
FIG. 8 is a top elevational schematic of the power train means.
Figure 9:
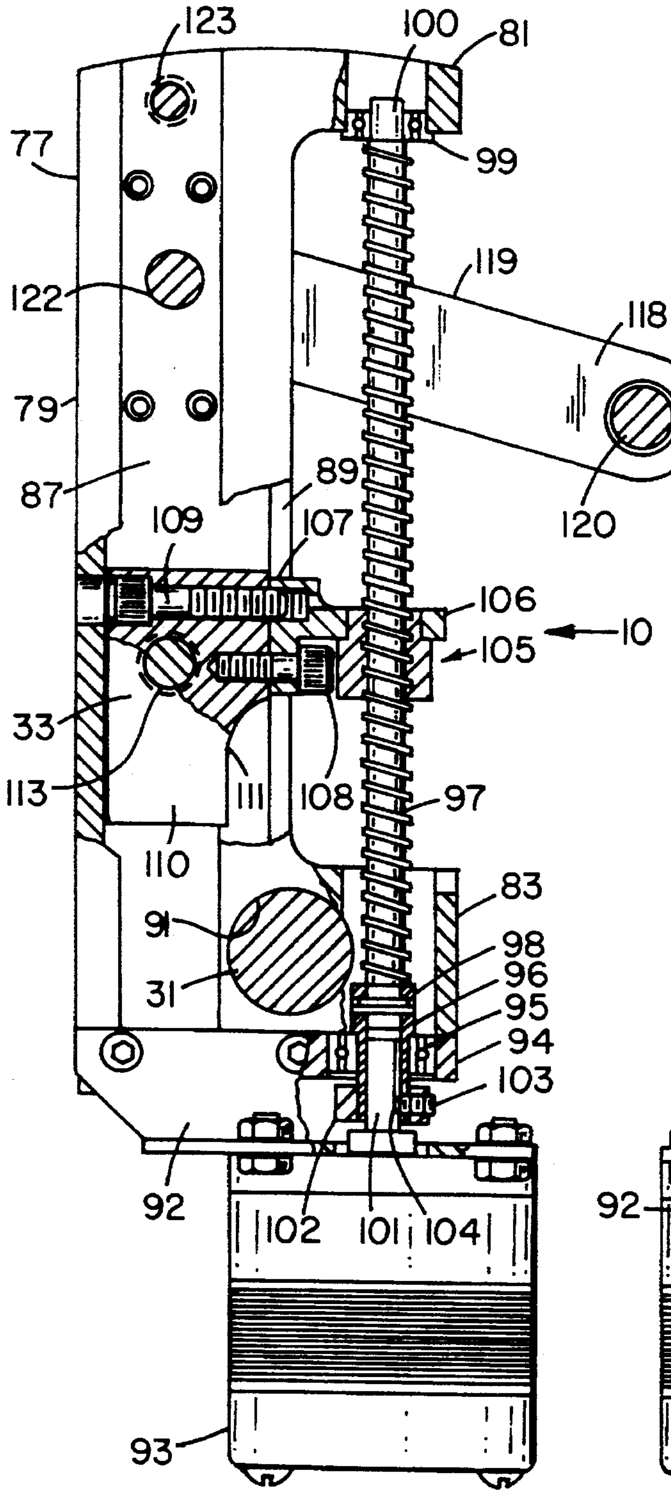
FIG. 9 is an enlarged, partially sectioned side view of the lift adjusting mechanism of the power train means.
Figure 10:
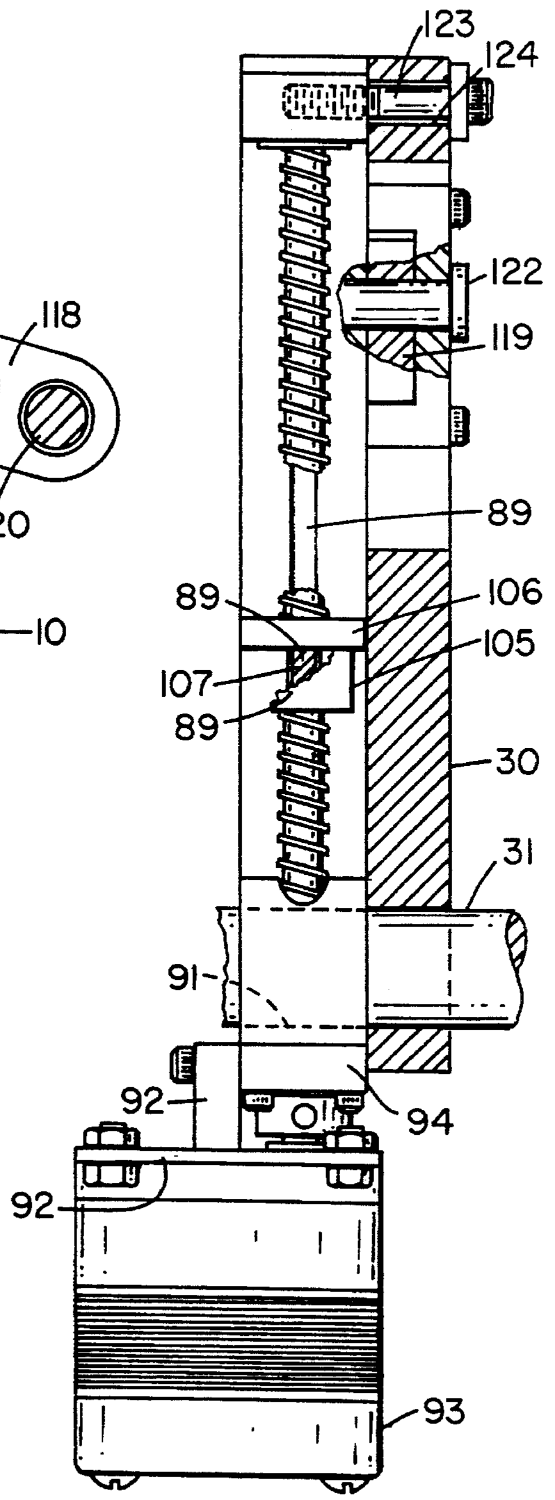
FIG. 10 is a partially sectioned front view of the adjusting mechanism of FIG. 9 taken in the direction of line 10 and showing portions of sector plate and asymetry adjustment link.
Figure 12:
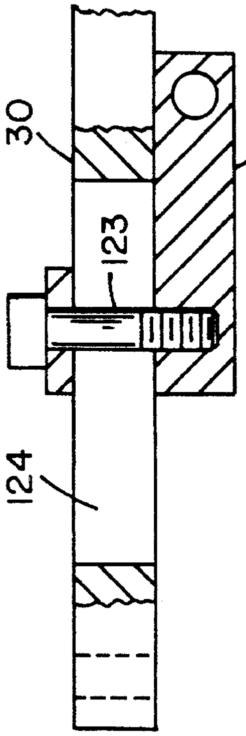
FIG. 12 is a sectional view of a portion of the sector plate taken along line 12—12 of FIG. 11 in the direction of the arrows.
Figure 17:
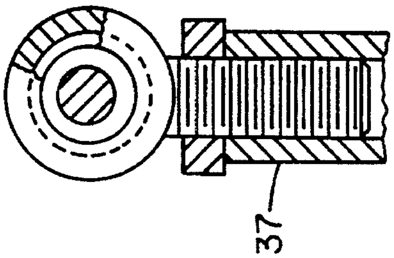
FIG. 17 is a cross-sectional view of a universal motion, self adjusting bushing type connector preferred for the various linking components of the present power train.

Referring particularly to FIGS. 9 and 10, the adjustable pivot means 33 preferably is incorporated in the variable crank member 77 which comprises body 79 having side extensions 81, 83, a side slot 87 (see FIGS. 8 and 9), a front or edge slot 89, a shaft receiving aperture 91, flange means 92 for supporting electric motor 93, bearing holder or cap 94, bearing 95, shaft coupling 96, lead screw 97 fixed by split pin 98 to said coupling, and top bearing 99 pressed into the aperture in extension 81 and having its inner race fixed to the top 100 of said screw. The shaft 101 of motor 93 is secured to said coupling by collar 102 and set screw 103 threaded through the collar and passing through aperture 104 in said coupling.

Pivot means 33 comprises a sliding nut comprising a threaded follower 105, a flange 106 having a narrow neck portion 107 vertically slidably mounted through edge slot 89. Neck portion 107 is affixed by screws 108, 109 to a slider block 110 which is vertically slidably mounted in side slot 87. A cut-out 111 allows the block to clear shaft 31 to allow maximum downward travel of nut 105. The said one end 37 of the swing link means 35 is pivotally mounted on said nut by screw 113.

Both the pivot means 33 and the variable crank member 77 act in concert with sector plate means 30 in that member 77 is connected to the sector plate by means of motor-gear reduction unit 114, the output shaft 116 which carries an eccentric 117 to which one end 118 of asymetry link 119, is pivotally connected by stud 120 or the like. The other end 121 of said link is pivotally connected to member 77 also by screw 122 or the equivalent. The sector plate and the variable crank member are otherwise independently rotatable around their axes such that the asymetry adjustment can be achieved i.e., the sector plate is preferably affixed to shaft 31 and member 77 is rotatable thereon and is held in proper position thereon by means of tubular spacer segments such as 134 mounted on said shaft between pillow blocks 115. The upper portion of member 77 is preferably provided with a bolt 123 or the like which is slidably through a curved slot 124 in the top of the sector plate in order to give lateral stability to both of these elements and to the asymetry ink 119.

Figure 13:
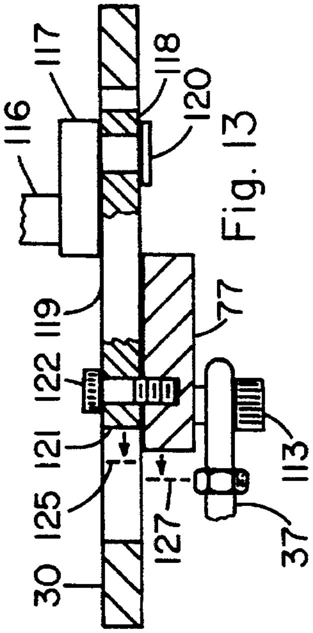
FIG. 13 is a sectional view of the sector plate taken along line 13—13 of FIG. 11 in the direction of the arrows and showing portions of the asymetry adjustment mechanism.
Figure 14:
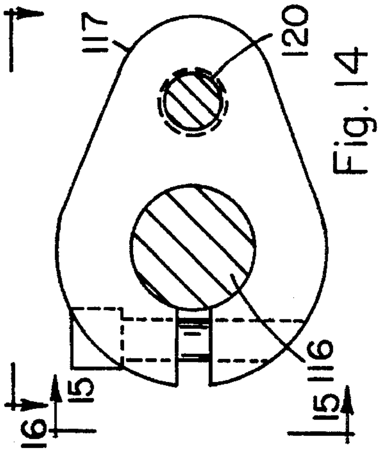
FIG. 14 is a side view of the asymetry crank.
Figure 11:
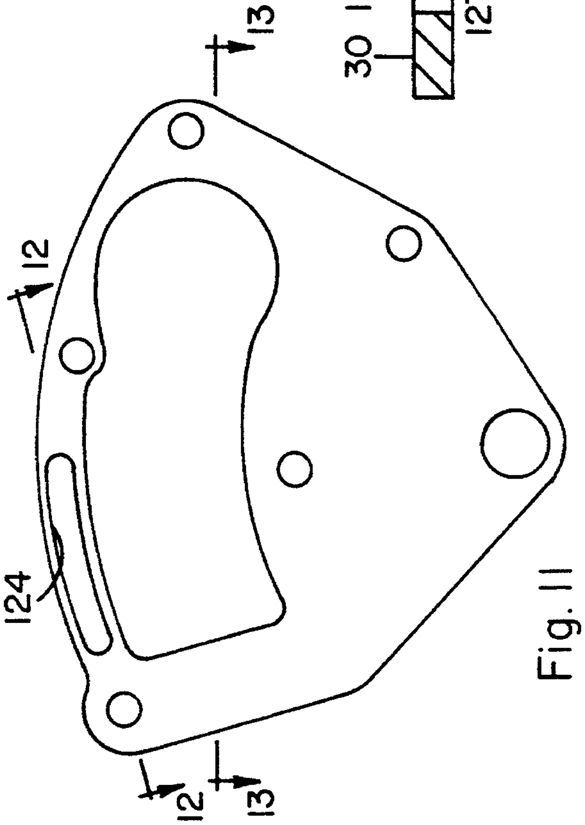
FIG. 11 is a side view of the sector plate of FIG. 7.
Figure 15:
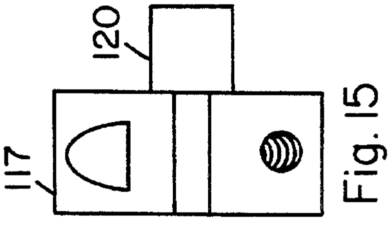
FIG. 15 is an end view of the asymetry crank taken in the direction of arrow 15 in FIG. 14.
Figure 16:
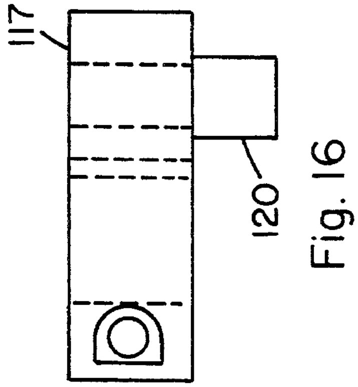
FIG. 16 is a top view of the asymetry crank taken in the direction of arrow 16 in FIG. 14.

In the operation of the present apparatus, the asymetry adjustment for body supports 12 and 14 is made by actuating unit 114 to rotate eccentric 117 a desired amount, e.g., ¼ turn from the position shown in the drawings to move link 119 to the left as shown in FIG. 13 by the dotted line 125 to also pivot member 77 to the left as shown by dotted line 127. Unit 114 is geared sufficiently low to allow controlled rotation of eccentric 117, e.g., 2–5 seconds for a 90 movement. This action moves swing link means 35 to the left in FIG. 1 and causes both lever means 39 and 48 to rotate in directions which move the first and second lift link means upwardly to position the body supports in a slightly up position with respect to the "HP" plane. This positioning causes asymetry in the travel of the body supports above and below the "HP" when the first power means 17 is actuated, i.e., the total pivotal travel of the body supports below the "HP" will be less than the total pivotal travel above the "HP". It is noted that where the eccentric 117 is initially set on the motor shaft 116 in a position 90 rotated from the position shown in the drawings, an equal asymetry both below and above the "HP" is selectable simply by rotating the eccentric either clockwise or counterclockwise the desired degree. It is further noted that lever means 39 is provided by two spaced segments 132, 133, however such construction is preferred only and is not essential.

The adjustment of the extent of pivotal travel of the body supports is made by actuating motor 93 to rotate lead screw 97 in the direction to either raise or lower pivot means 33. Since member 77 pivots about shaft means 31, lowering pivot means 33 will reduce the travel of swing link means 35 and of the lift link means 45 and 67.

Also mounted to the base floor or tubing sections such as the lateral tubing sections 75 or the like is the first power means 17 which comprises, e.g., a worm-gear reduction unit and electric motor. The reduction unit should have an input to output speed ratio of at least about 15:1 to about 200:1 or greater. This reduction, achieved by using worm-gears, provides the constant inertial drag of at least about 150 pounds as measured at the lift point, i.e., 126 of each body support means.

Figure 5:
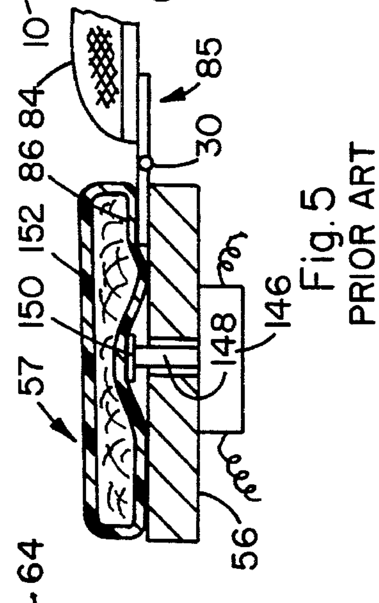
Fig. 5 PRIOR ART
Figure 4:
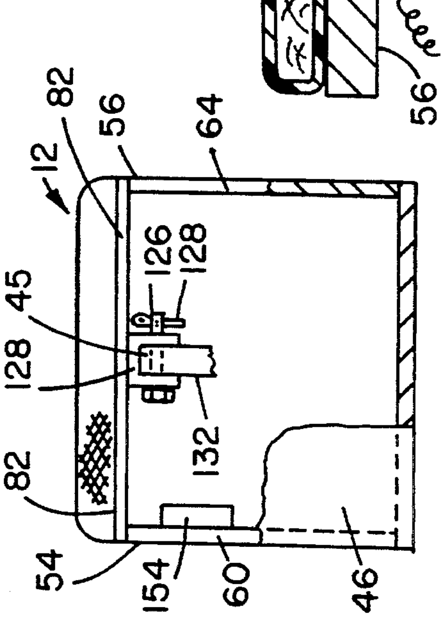
Fig. 4 PRIOR ART
Figure 7:
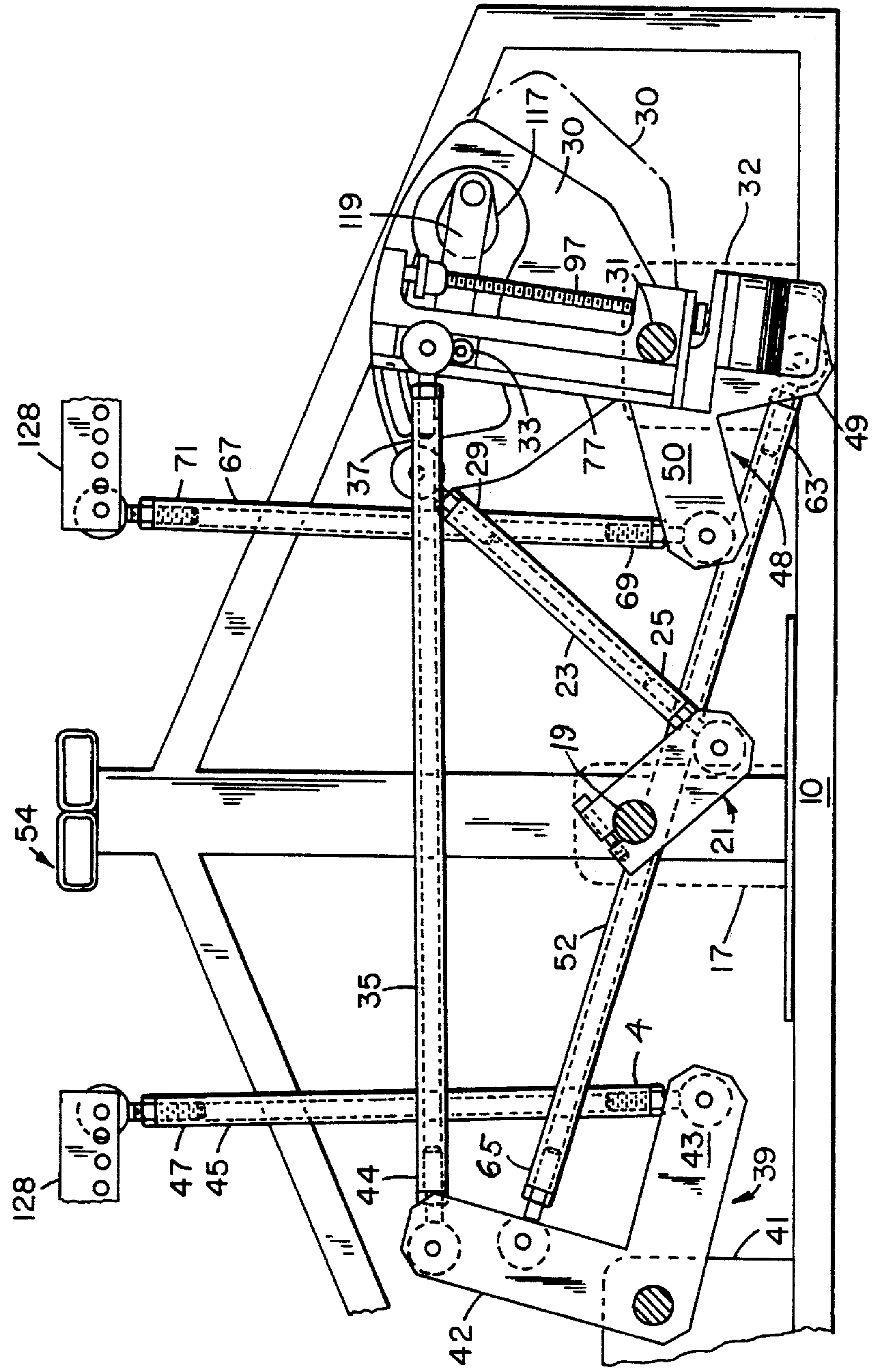
FIG. 7 is a side view as in FIG. 1 but showing the power train means in greater detail.

Referring to FIG. 5, one or more electrical switching mechanisms such as 146 are mounted on lateral or back segment support member 56, preferably in at least one location where substantial body weight is certain to be applied during treatment. The actuating plunger 148 of the switch slidably extends through member 56 and is provided with a lead 150 for contacting the underside of the covering 152 of pad 57 such that significant body weight will depress the plunger and activate an electrical circuit. This switching device is intended to actuate an electrically operated counter device only when a patient is actually on the body supports. The counter device is mounted, e.g., in a locked box 154 on the inside of the base sidewall, and accessible only to an attending physician, medical technician or the like for reading the number of rotative cycles of the body supports actually experienced by the patient. In a preferred embodiment, an elapsed time recorder is associated with the circuit to record the total elapsed time that the patient has been subjected to the passive motion. For example, a typical treatment period would be fifteen minutes at 4.0 cycles per minute, twice a day.

The drive or power means of the apparatus may be provided with a variable speed feature in known manner, and with a control mechanism including on-off switching, mounted, e.g., on the side of the apparatus on a control panel such as 156. Also, any remote or equivalent control system, such as a control cord and switch box may be employed, e.g., for patients who have great difficulty in moving and must have the control box in a readily accessible location, e.g., the immediate vicinity of their hand.

In a preferred embodiment of the present invention, as shown in FIG. 18, an additional safety feature is provided which supplements the elimination of the reverse action of the drive means. This safety feature comprises a position responsive switch for the electrical circuit of the drive train. This switch can sense certain irregular motion of the body support means and instantly cut off power to the drive train.

This switch comprises means associated with each body support 12 and 14 which senses the arc angle or vertical position of its associated body support and terminates, i.e., switches off power to the drive train if the body support is in an irregular position at a particular time.

Figure 19:
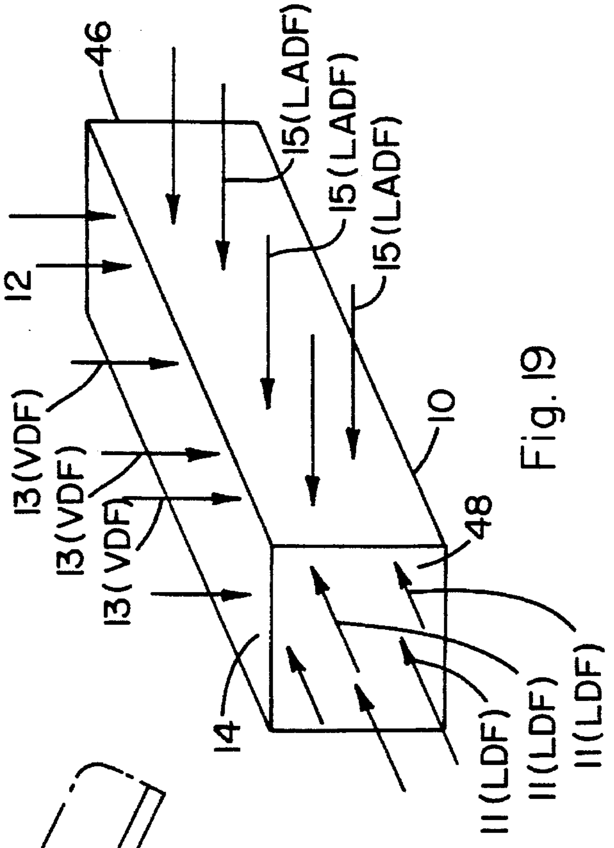
FIG. 19 is a schematic outline of the present apparatus showing the longitudinal directional field "LDF", the lateral directional field "LADF", and the vertical directional field "VDF"

Referring to FIG. 19, an operable but only exemplary embodiment of the safety switch is shown as comprising, preferably, a low votage source such as rechargeable 6 volt battery 216 mounted on a portion of base 10 and connected to the resistive coil or carbon track of a potentiometer 217 by leads 218, 219, and a moving contact 220 having a non-conducting arm 221 attached at one end to bed member 82 and provided at its other end with a conducting segment 222 having a conducting roller contact 223 mounted thereon. Base 217 is provided with suitable spring means 226 which continually urges the potentiometer coil or track into contact with roller contact 223 throughout the full arcuate travel thereof.

In operation of the above safety device which is provided for each body support, the leads 224, 225 across which the potentiometer resistance is measured are connected into suitable electronic equipment such as a microprocesser unit which is preprogrammed with a desired motion or cycle patten and speed for each body support. In the event that either roller contact is in the wrong position at the wrong-time, or is moving too fast along the potentiometer, the microprocesser signals suitable switching means to terminate power to the drive train.

It is particularly noted that other position responsive switch safety means may be employed, although perhaps less effectively, such as mercury switches mounted on each body support and electrically interconnected such that they would terminate power to the drive train in the event that both body supports, for example, were not at substantially the same angle with respect to the horizontal. Such a level switch is mounted, for example, to each body support such that when one is open, the other is closed and vice versa. As the supports pass through horizontal, the switches reverse such that they are both closed at level and reverse as the supports pass through the horizontal plan. The switches are wired to a relay which will shut down the motor if opened. The theory is that the apparatus will operate as long as both supports are in sync, but will open the relay if either support stops functioning. This shut-off will occur, preferably, as the non-functioning support passes through horizontal.

It is noted that the operations of the present drive train components and safety devices are all preferably integrated into a computer program system which can be readily updated as the patient progresses, to allow, for example, more energetic exercise toward the end of the treatment period. The electrical circuitry necessary for operating the various worm-gear reducers and the like are readily adaptable by means well known to the electronics art such that a computer program for their operation can readily be developed for fully automating the present body motion device.

It is further noted that the terms "inertial, reverse arrest drag", or "arrest drag" as used herein, refer to the weight that would be required to be applied downwardly on a body support means as measured with power off to the prime mover of the power train means and at the point or pivot of the lift link or other means which actually contacts the bottom of the body support means to apply lifting or rotative force thereto, in order to overcome frictional forces and reverse the operation of the power train means and cause the body support means to pivot downwardly in an uncontrolled manner. In this regard, a worm-gear reduction unit or a screw/nut combination of the proper pitch will inherently, i.e., in their normal lubricated condition, provide the necessary arrest drag. It is noted that one skilled in the art should select the reduction or adjustment mechanisms which has an adequate reduction ratio or thread pitch to provide at least the aforesaid minimum arrest drag.

The invention has been described in detail with particular reference to preferred embodiments thereof, but it will be understood that variations and modifications will be effected within the spirit and scope of the invention.

I claim:

1. A passive body-motion generating apparatus for a lumbar region:, back segment, comprising base means, lower body support means, upper body support means, the top of each said support means providing body contact surface means, a stationary, substantially flat lumbar region, back segment support means on said base means lying intermediate said pivot end portions, said back segment support means having a width of from about 2 to about 12 inches, said body support means each having a pivot end portion lying substantially adjacent an opposite side of said back segment support means, pivot means cooperatively mounted on each said pivot end portion and said base means for allowing independent rotative motion of each said lower and upper body support means through an arc sector, the pivot axes of said pivot means being substantially parallel, and bearing mounted power train means on said base means, linkage means pivotally mounted on said apparatus for pivotal motion with respect to said base means and both said body support means for imparting simultaneous rotative force to said both support means, said power train means having a longitudinal directional field, a vertical directional :field and a lateral directional field and comprising first power means mounted on said apparatus and having drive shaft means, drive crank arm means affixed to said shaft means, crank link means having one end pivotally connected to said crank arm means and its other end pivotally connected to sector plate means, said plate means being pivotally mounted on said apparatus, adjustable pivot means mounted on said plate means for position adjustment within each of said longitundinal and vertical directional fields, swing link means having one end pivotally connected to said adjustable pivot means, first lever means pivotally mounted on said apparatus and having a first driven arm means and a first drive arm means, the other end of said swing link means being pivotally connected to said driven arm means, first lift link means having one end pivotally connected to said first drive arm means and having its other end pivotaly connected to one of said lower or upper body support means, second lever means pivotally mounted on said apparatus and having a second driven arm means and a second drive arm means, drag link means having one end pivotally connected to said second drive arm means and having its other end pivotally connected to said first driven arm means, and second lift link means having one end pivotally connected to said second drive arm means and having its other end pivotally connected to the other of said lower or upper body support means, wherein the pivot axes of all of said pivotal connections are within said lateral directional field.

2. The apparatus of claim 1 wherein said first power means is provided with motion resistance means giving a constant inertial, reverse arrest drag of at least about 150 pounds as measured at the lift point of each said body support means.

3. The apparatus of claim 1 wherein the adjustable pivot means comprises a thread nut which is slidably mounted within a substantially vertical track support on said sector plate means and which is movable within said track support by electrically operated second power means.

4. The apparatus of claim 1 wherein the track support is adjustably mounted on said sector plate means for adjustment substantially within said longitudinal component.

5. The apparatus of claim 1 wherein the motion of adjustment of said track support on said sector plate means is along a segment of the pivotal arc of said sector plate.

* * * * *